(12) United States Patent
Iijima

(10) Patent No.: US 11,969,284 B2
(45) Date of Patent: Apr. 30, 2024

(54) RADIOGRAPHIC IMAGING APPARATUS, METHOD OF CONTROLLING THE SAME, RADIOGRAPHIC IMAGING SYSTEM, AND STORAGE MEDIUM

(71) Applicant: CANON KABUSHIKI KAISHA, Tokyo (JP)

(72) Inventor: Tadahiko Iijima, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 279 days.

(21) Appl. No.: 17/482,199

(22) Filed: Sep. 22, 2021

(65) Prior Publication Data

US 2022/0096035 A1    Mar. 31, 2022

(30) Foreign Application Priority Data

Sep. 25, 2020  (JP) ................................. 2020-160942

(51) Int. Cl.
*A61B 6/00* (2006.01)
*G01N 23/04* (2018.01)

(52) U.S. Cl.
CPC .................. *A61B 6/54* (2013.01); *A61B 6/56* (2013.01); *G01N 23/04* (2013.01); *G01N 2223/306* (2013.01)

(58) Field of Classification Search
CPC .. A61B 6/548; A61B 6/56; A61B 6/54; A61B 2560/0209; A61B 6/542; A61B 6/467; G03B 42/02; H05G 1/30
See application file for complete search history.

(56) References Cited

U.S. PATENT DOCUMENTS

2005/0207534 A1* 9/2005 Petrick ................. G01T 1/2985
378/114

FOREIGN PATENT DOCUMENTS

| JP | 2002165142 A | 6/2002 |
|---|---|---|
| JP | 2002272720 A | 9/2002 |

\* cited by examiner

*Primary Examiner* — Don K Wong
(74) *Attorney, Agent, or Firm* — Canon U.S.A., Inc. IP Division

(57) ABSTRACT

A radiographic imaging apparatus includes a state transition mode selection unit configured to select a state transition mode from among a first state transition mode of changing from a stand-by state to a ready-for-imaging state based on irradiation preparation start information about a radiation generation apparatus and a second state transition mode of changing from the stand-by state to the ready-for-imaging state based on other information excluding the irradiation preparation start information.

12 Claims, 11 Drawing Sheets

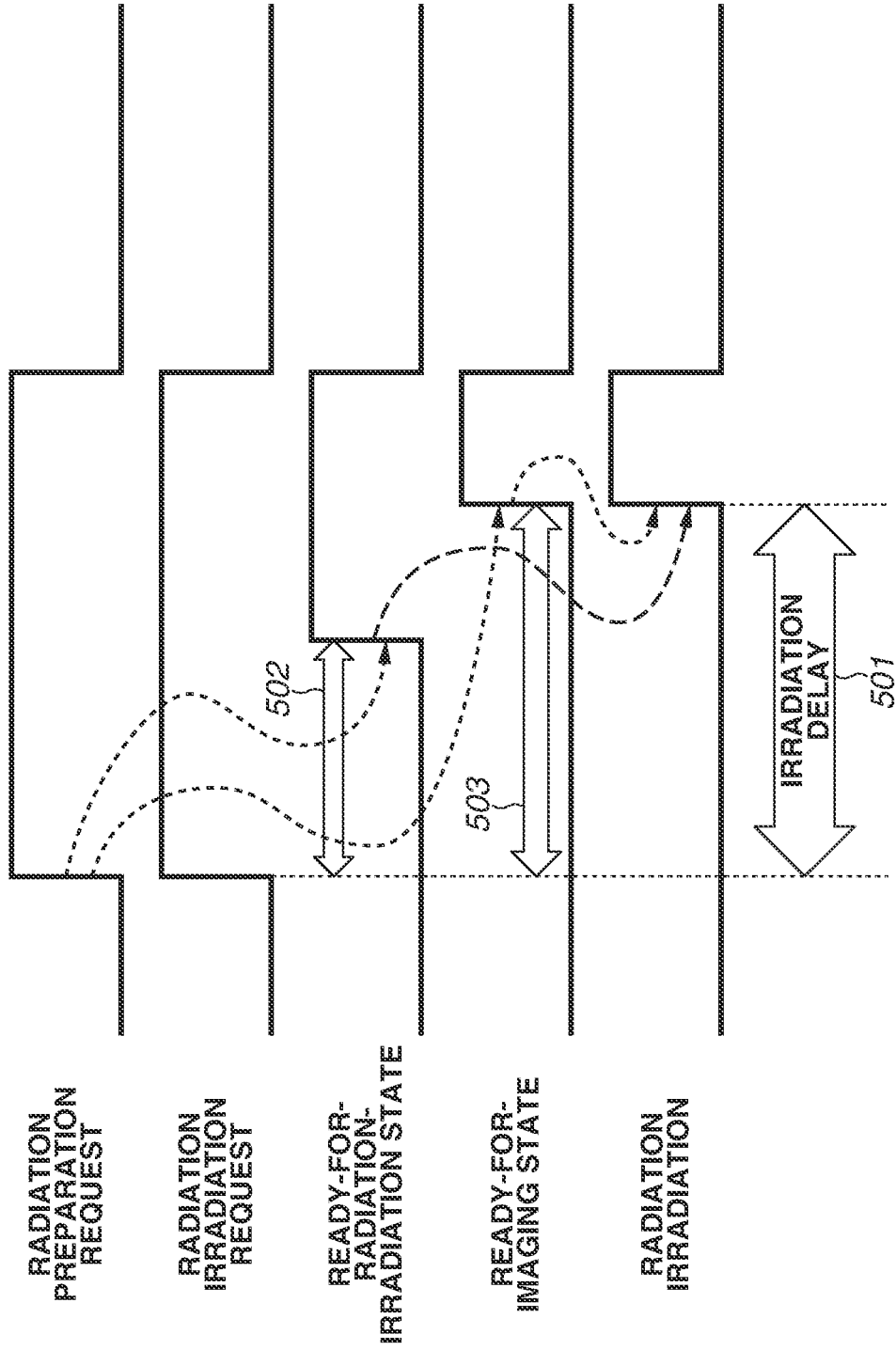

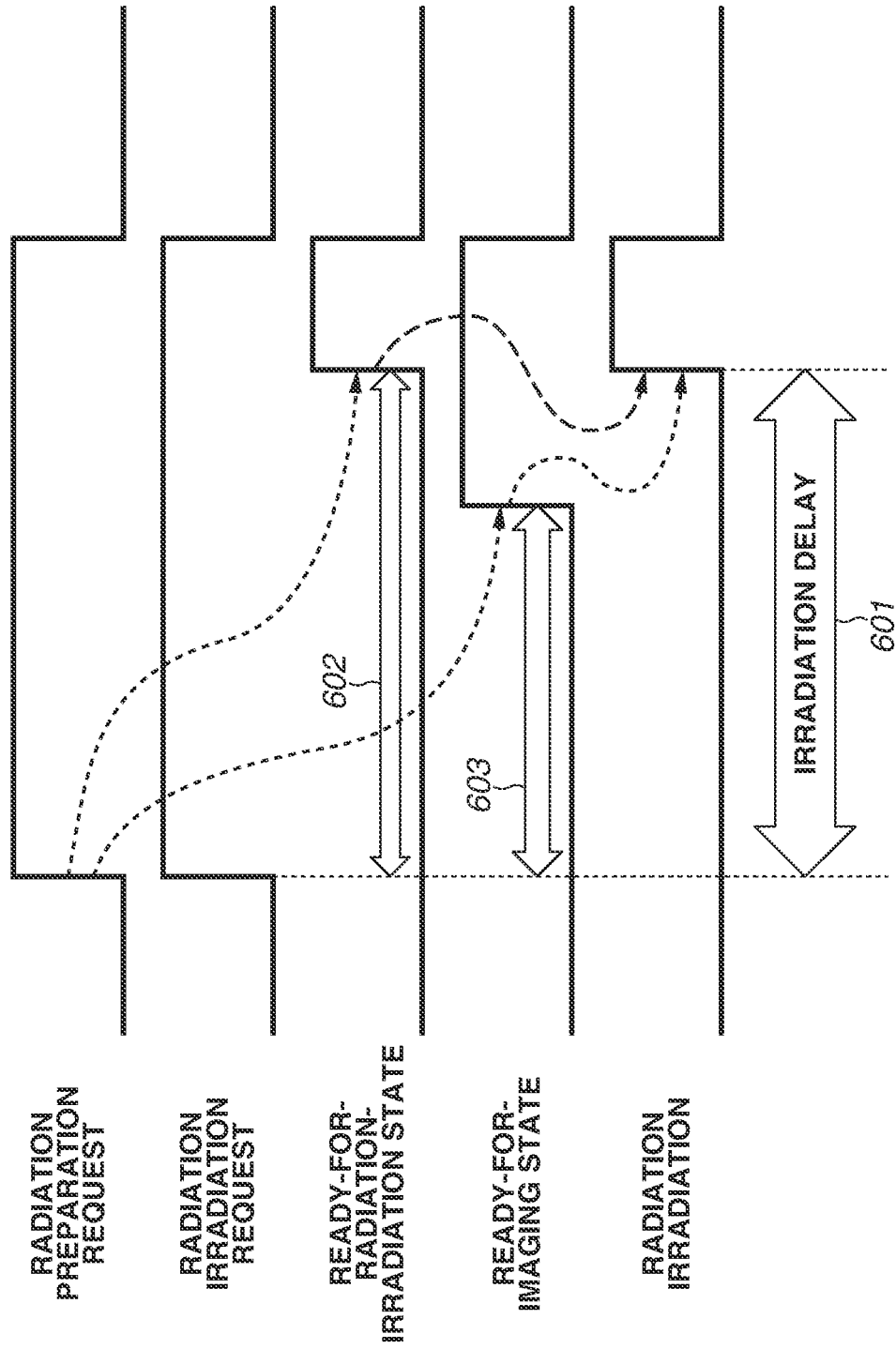

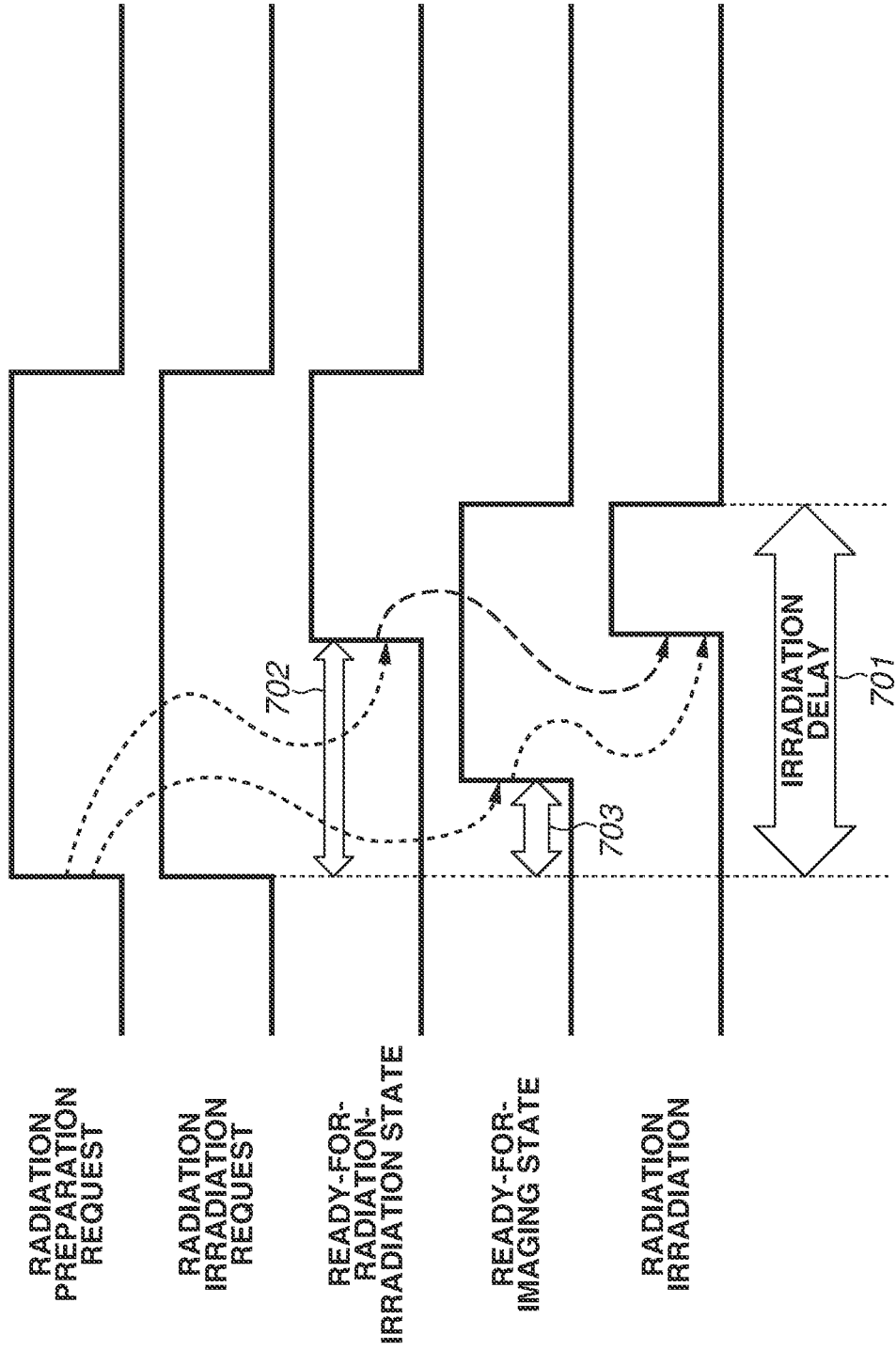

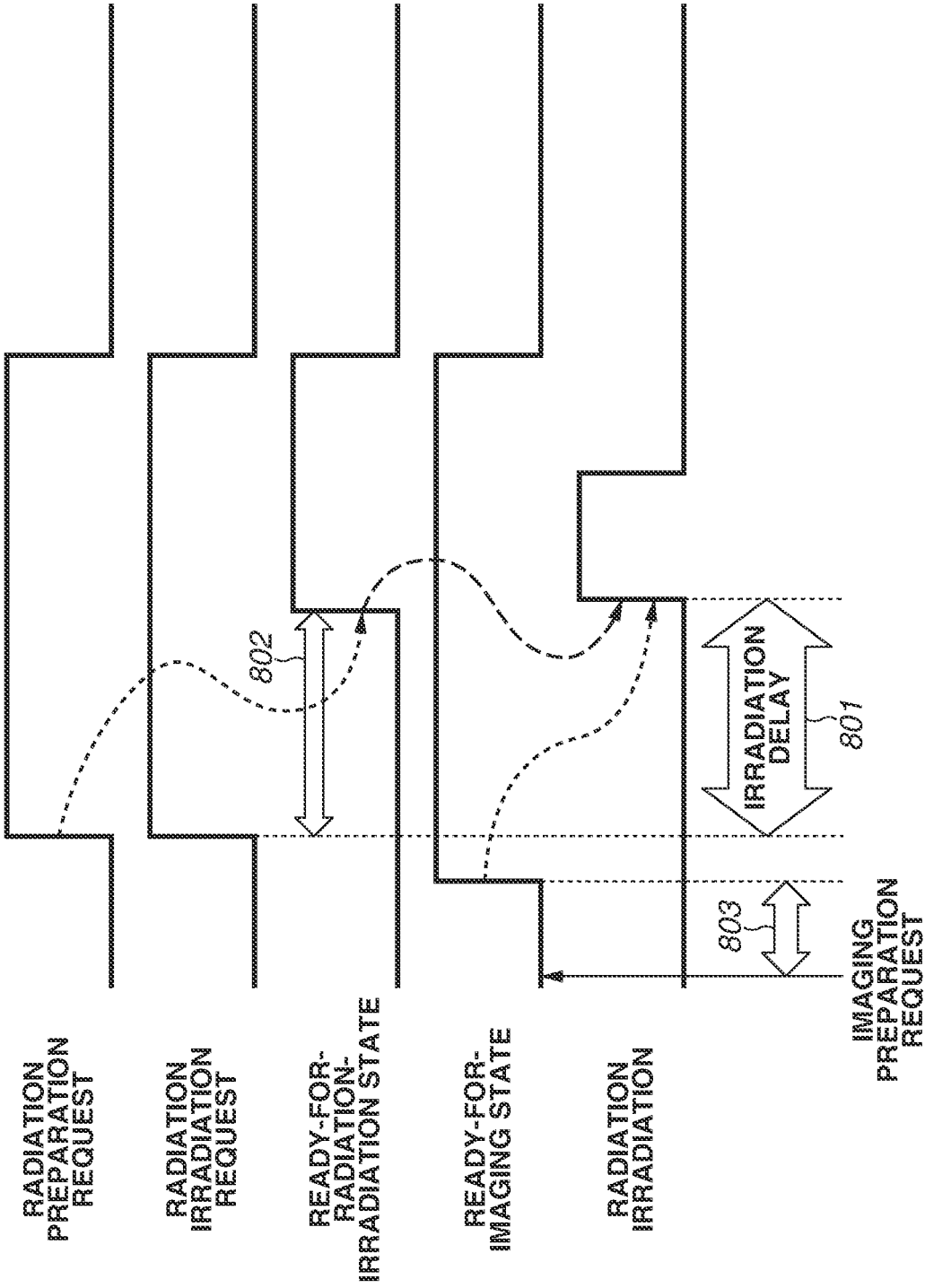

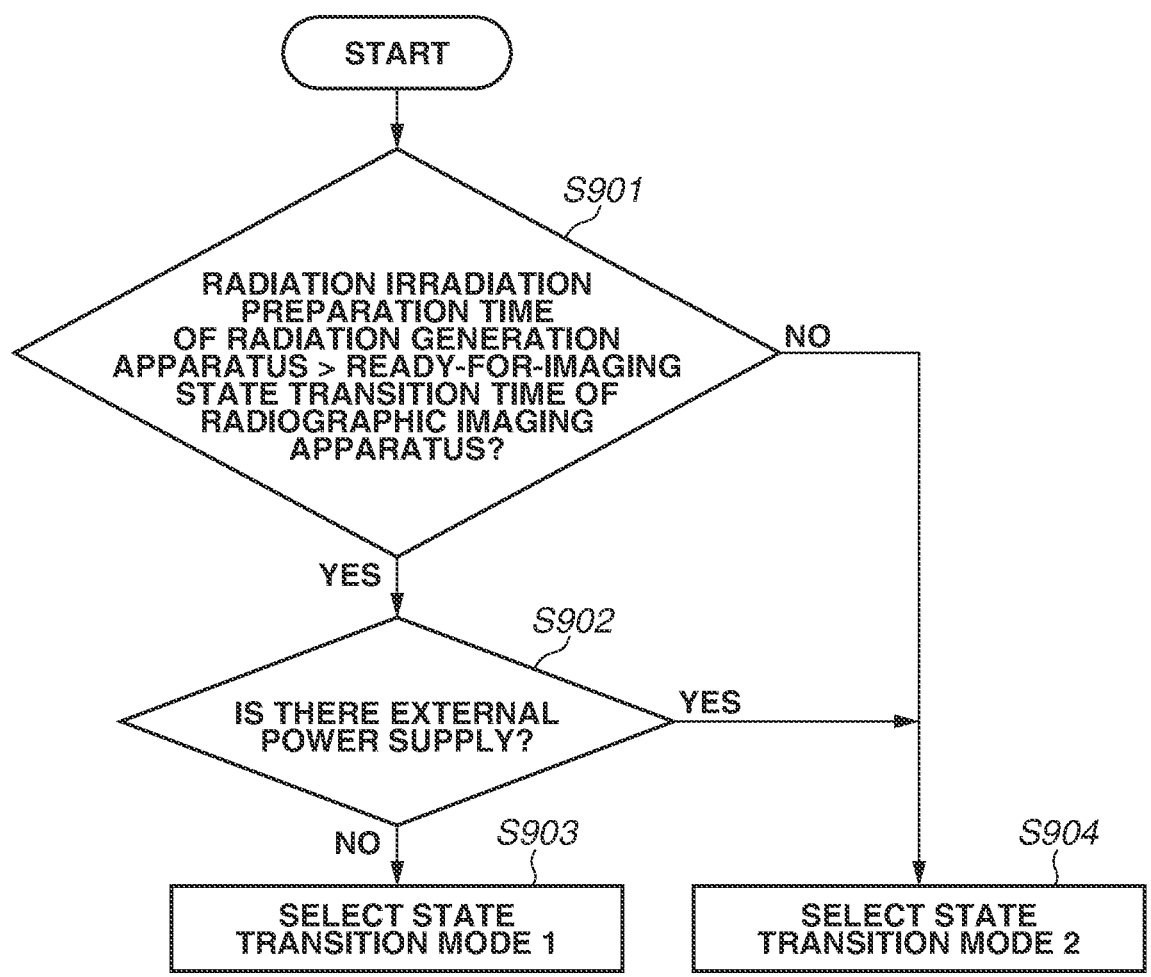

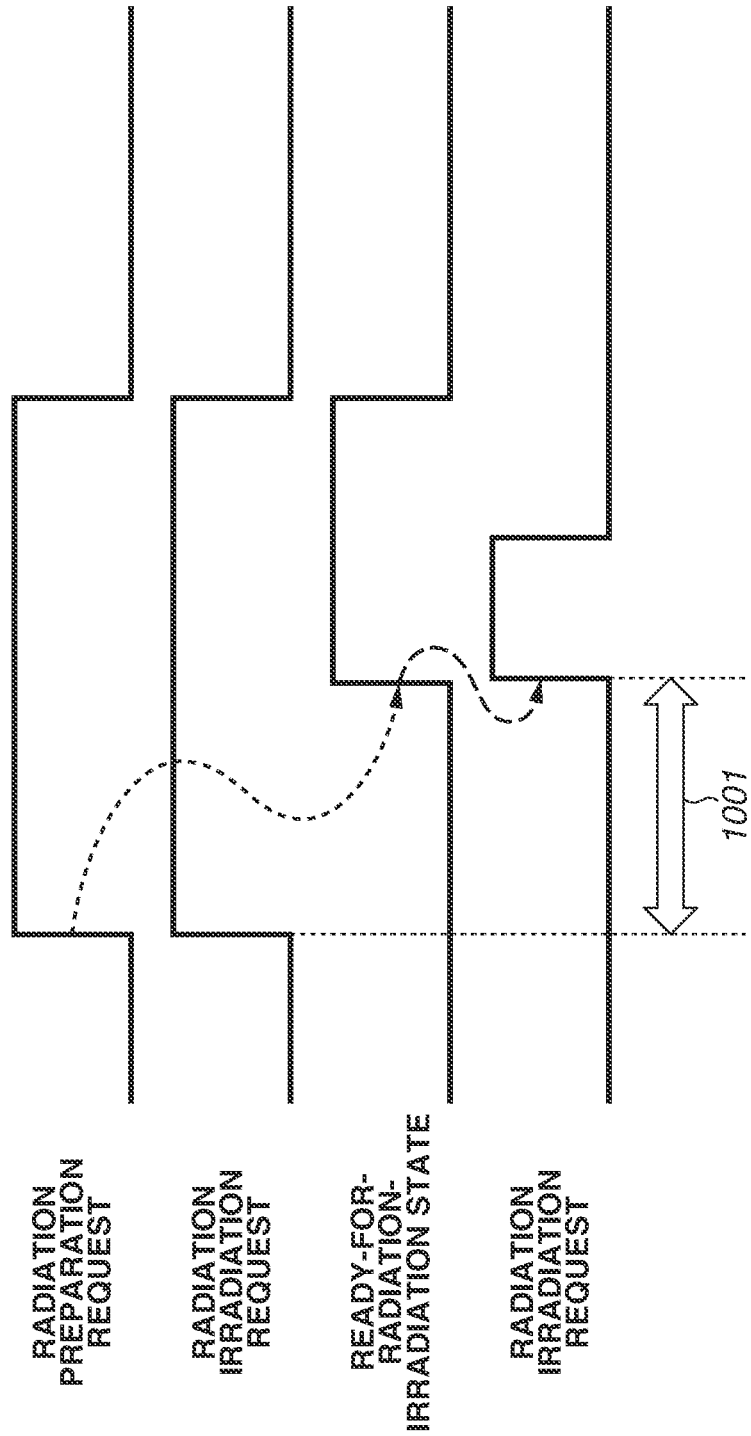

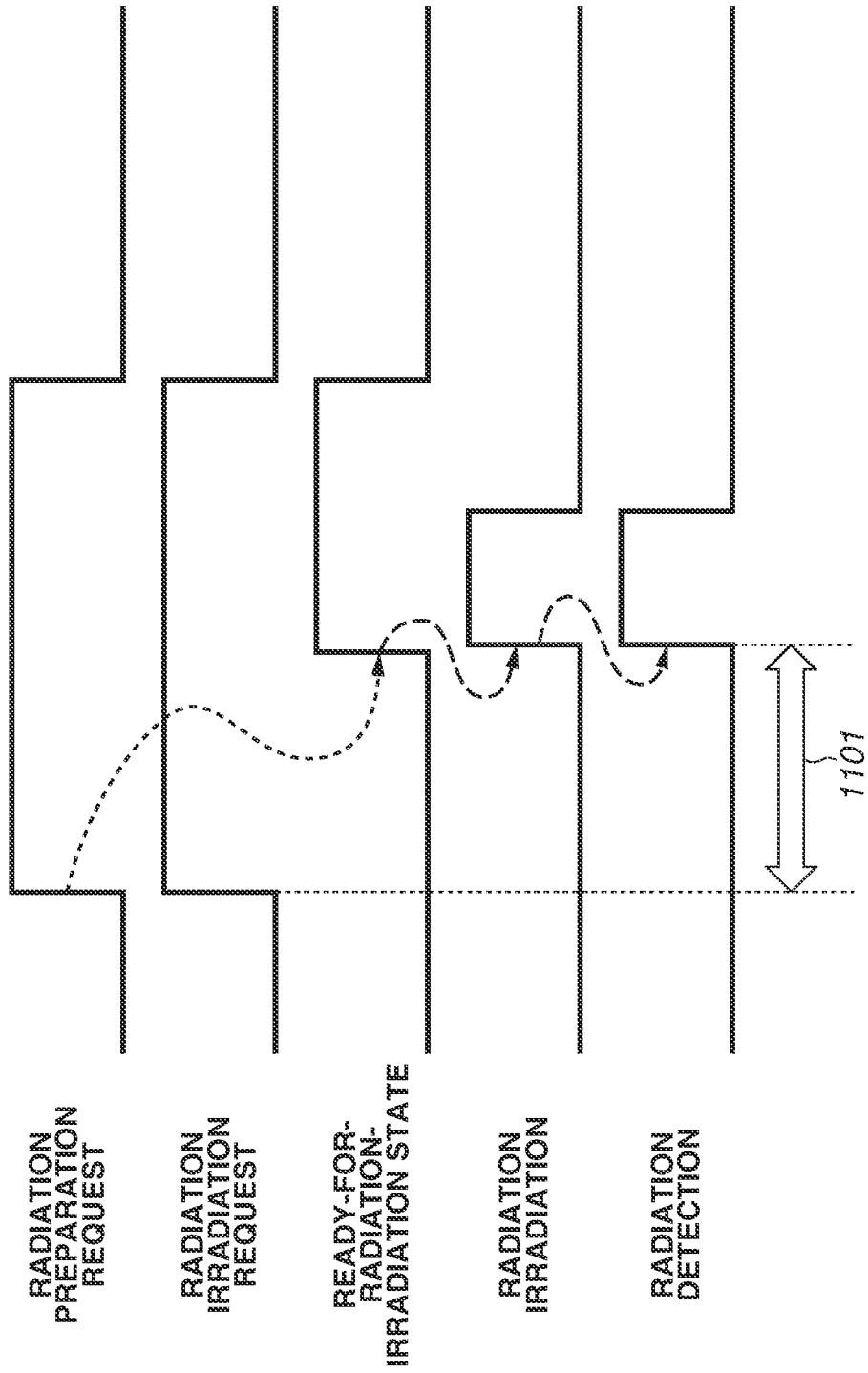

RADIOGRAPHIC IMAGING APPARATUS, METHOD OF CONTROLLING THE SAME, RADIOGRAPHIC IMAGING SYSTEM, AND STORAGE MEDIUM

BACKGROUND

Field

The present disclosure relates to a radiographic imaging apparatus configured to perform radiographic imaging, a method of controlling the same, a radiographic imaging system, and a storage medium for causing a computer to function as a radiographic imaging apparatus.

Description of the Related Art

In recent years, digitalization of radiographic imaging systems has been advanced as a result of development of radiographic imaging apparatuses that generate digital radiographic images based on incident radiation. The digitalization of radiographic imaging systems makes it possible to check a radiographic image immediately after radiographic imaging, and this significantly improves a workflow compared to conventional imaging methods that use films or computed radiography (CR) apparatuses.

Furthermore, wireless radiographic imaging apparatuses have been developed, and this facilitates use of radiographic imaging apparatuses. Wireless radiographic imaging apparatuses use a battery to operate, and thus the number of images that can be captured per charge leads to ease of use. In order to increase the number of images that can be captured, power consumption of a radiographic imaging apparatus needs to be decreased. Since a digital radiographic imaging apparatus is changed to a ready-for-imaging state after a stand-by state in which power consumption is lower than that in the ready-for-imaging state is cancelled, a user has to wait for a predetermined waiting time. Regarding the stand-by state cancellation, because a shorter time before imaging is desirable for a person capturing an image of a patient and also for the patient, Japanese Patent Application Laid-Open No. 2002-165142 discusses a plurality of stand-by state cancellation methods, and Japanese Patent Application Laid-Open No. 2002-272720 discusses a method of cancelling the stand-by state based on input of an imaging order.

In the plurality of stand-by state cancellation methods discussed in Japanese Patent Application Laid-Open No. 2002-165142, an issue arises in that, for example, a stand-by state cancellation method that is high in power consumption may be selected even when a waiting time before irradiation with radiation is the same as the other methods.

The method, discussed in Japanese Patent Application Laid-Open No. 2002-272720, of cancelling the stand-by state based on input of an imaging order has also an issue that power consumption increases if a time from input of an order to imaging increases.

SUMMARY

Various embodiments of the present disclosure provide a system of selecting a stand-by state cancellation method that is optimum in terms of power consumption, in a ease where there is a plurality of stand-by state cancellation methods in a radiographic imaging apparatus.

According to one embodiment of the present disclosure, a radiographic imaging apparatus is provided which includes an image generation unit configured to generate a radiographic image based on incident radiation. The radiographic imaging apparatus includes a reception unit configured to receive irradiation preparation start information about a start of preparation for irradiation with the radiation in a radiation generation apparatus that generates the radiation, and a selection unit configured to select a state transition mode from among a first state transition mode of changing from a stand-by state to a ready-for-imaging state based on the irradiation preparation start information and a second state transition mode of changing from the stand-by state to the ready-for-imaging state based on other information excluding the irradiation preparation start information, the selection unit selecting the state transition mode based on a state transition characteristic in changing from the stand-by state in which power consumption is lower than power consumption in the ready-for-imaging state to the ready-for-imaging state in the radiographic imaging apparatus and a radiation irradiation characteristic in changing to a ready-for-radiation-irradiation state in the radiation generation apparatus.

Embodiments of the present disclosure include a method of controlling the above-described radiographic imaging apparatus, a radiographic imaging system including the above-described radiographic imaging apparatus, and a storage medium storing a program for causing a computer to function as each unit of the above-described radiographic imaging apparatus.

According to one embodiment of the present disclosure, a stand-by state cancellation method that is optimum in terms of power consumption is selected, in a case where there is a plurality of stand-by state cancellation methods in a radiographic imaging apparatus.

Further features of the present disclosure will become apparent from the following description of example embodiments with reference to the attached drawings.

BRIEF DESCRIPTION OF THE DRAWINGS

FIG. 5 is a diagram illustrating an example of a timing chart of a case where a radiation irradiation preparation time is shorter than a ready-for-imaging state transition time according to a comparative example.

FIG. 6 is a diagram illustrating an example of a timing chart of a case where the radiation irradiation preparation time is longer than the ready-for-imaging state transition time in the radiographic imaging system according to the first example embodiment.

FIG. 7 is a diagram illustrating an example of a timing chart of a case where a radiographic imaging apparatus with a short ready-for-imaging state transition time is used in the radiographic imaging system according to the first example embodiment.

FIG. 8 is a diagram illustrating an example of a timing chart of a case where a radiographic imaging apparatus with a long ready-for-imaging state transition time is used in the radiographic imaging system according to the first example embodiment.

FIG. 9 is a flowchart illustrating an example of a method of controlling a radiographic imaging apparatus according to a second example embodiment.

FIG. 10 is a diagram illustrating an example of a timing chart of a radiographic imaging system according to a third example embodiment.

FIG. 11 is a diagram illustrating an example of a timing chart of a radiographic imaging system according to a fourth example embodiment.

DESCRIPTION OF THE EMBODIMENTS

Various example embodiments of the present disclosure will be described below with reference to the drawings. The below-described example embodiments of the present disclosure are not intended to limit the scope of the claimed invention, and not all combinations of features described in the example embodiments of the present disclosure are always essential to a technical solution of the present invention. While use of X-rays as radiation in the example embodiments of the present disclosure is desirable, the present invention is not limited to those disclosed herein, and other types of radiations, such as α-rays, β-rays, or γ-rays are also applicable to the present invention.

Figure 1:
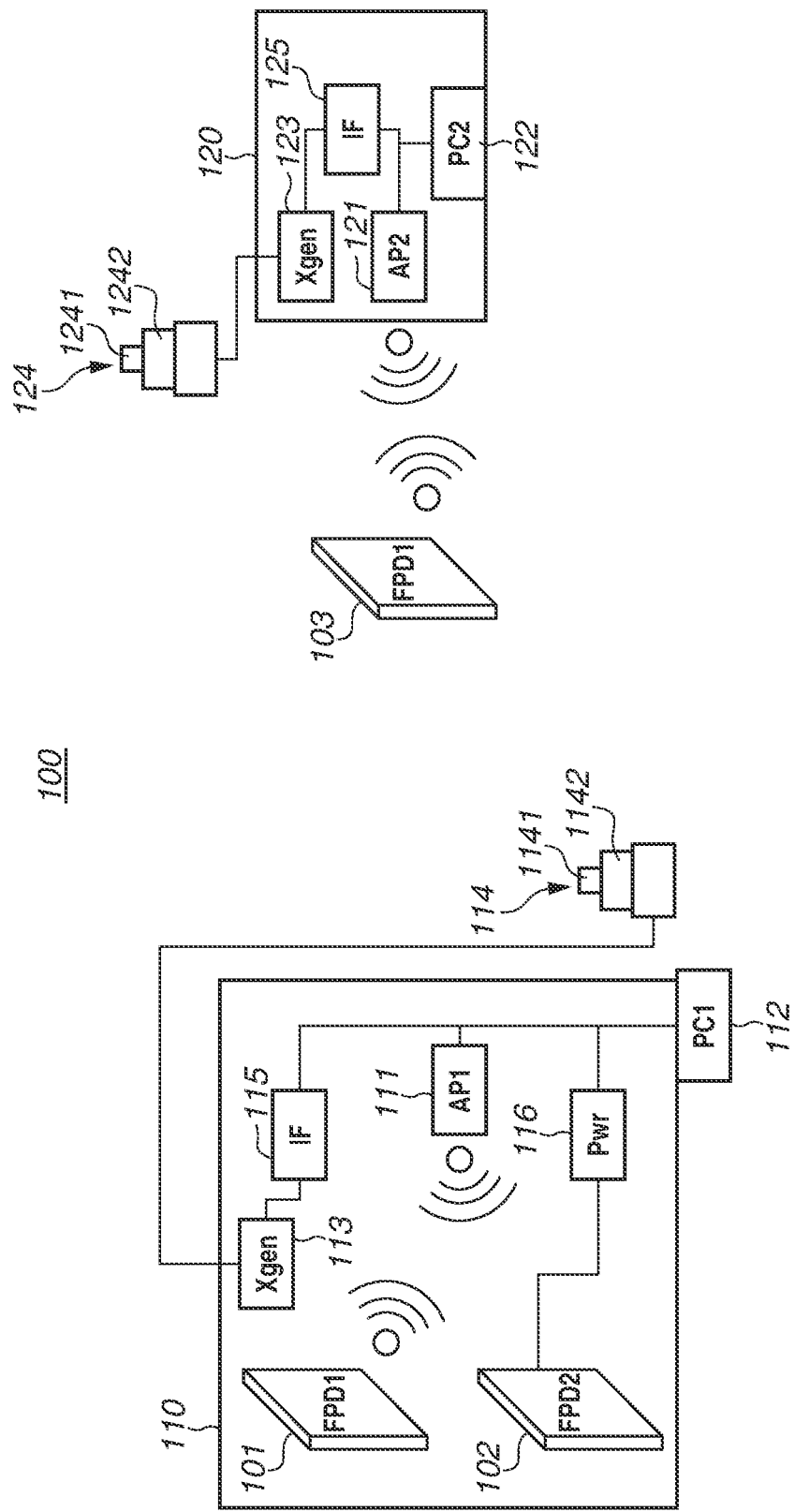
FIG. 1 is a diagram illustrating an example of a schematic configuration of a radiographic imaging system according to a first example embodiment.

First, a first example embodiment of the present disclosure will be described below. FIG. 1 is a diagram illustrating an example of a schematic configuration of a radiographic imaging system 100 according to the first example embodiment of the present disclosure. The radiographic imaging system 100 according to the present example embodiment includes components disposed at a radiographic imaging room 110 and components disposed at an instrument carriage 120.

Radiographic imaging apparatuses 101 and 102 are radiographic imaging apparatuses disposed at the radiographic imaging room 110 (specifically, the radiographic imaging apparatuses 101 and 102 are installed in the radiographic imaging room 110). A radiographic imaging apparatus 103 is a radiographic imaging apparatus disposed at the instrument carriage 120 and, for example, the radiographic imaging apparatus 101 can be moved and used as the radiographic imaging apparatus 103. Each of the radiographic imaging apparatuses 101 to 103 can use a battery or external power supply to operate.

At the radiographic imaging room 110, a wireless access point 111 ("AP1" in FIG. 1), a console 112 ("PC1" in FIG. 1), a radiation generation apparatus 113 ("Xgen" in FIG. 1), a radiation switch 114, a repeater 115 ("IF" in FIG. 1), and a power supply apparatus 116 ("Pwr" in FIG. 1) are disposed in addition to the radiographic imaging apparatuses 101 and 102. The console 112 controls the radiographic imaging apparatuses 101 and 102. The repeater 115 adjusts timings between the radiographic imaging apparatuses 101 and 102 and the radiation generation apparatus 113. The radiation switch 114 includes a radiation preparation request switch 1141 and a radiation irradiation request switch 1142. The radiation preparation request switch 1141 issues an instruction to request a start of preparation for radiation irradiation to the radiation generation apparatus 113. The radiation irradiation request switch 1142 issues an instruction to request radiation irradiation to the radiation generation apparatus 113. The radiation preparation request switch 1141 and the radiation irradiation request switch 1142 are a two-step switch, and the radiation preparation request switch 1141 is pressed always before the radiation irradiation request switch 1142. The power supply apparatus 116 is an apparatus configured to supply power (electric power) to a radiographic imaging apparatus (e.g., the radiographic imaging apparatus 102 in FIG. 1). The power supply apparatus 116 includes an interface for not only power supply but also wired communication and can relay communication between the radiographic imaging apparatus and a communication apparatus. The radiographic imaging apparatus 101 uses a battery to operate and transmits a radiographic image to the console 112 via wireless communication with the wireless access point 111. The radiographic imaging apparatus 102 is connected to the power supply apparatus 116 and operates using the external power supply to perform wired communication.

At the instrument carriage 120, a wireless access point 121 ("AP2" in FIG. 1), a console 122 ("PC2" in FIG. 1), a radiation generation apparatus 123 ("Xgen" in FIG. 1), a radiation switch 124, and a repeater 125 ("IF" in FIG. 1) are disposed in addition to the radiographic imaging apparatus 103. The console 122 controls the radiographic imaging apparatus 103. The repeater 125 adjusts timings between the radiographic imaging apparatus 103 and the radiation generation apparatus 123. The radiation switch 124 includes a radiation preparation request switch 1241 and a radiation irradiation request switch 1242. The radiation preparation request switch 1241 issues an instruction to request a start of preparation for radiation irradiation to the radiation generation apparatus 123. The radiation irradiation request switch 1242 issues an instruction to request radiation irradiation. The radiation preparation request switch 1241 and the radiation irradiation request switch 1242 are a two-step switch similar to the radiation preparation request switch 1141 and the radiation irradiation request switch 1142. In a case where the radiographic imaging apparatus 103 is used with the instrument carriage 120, the radiographic imaging apparatus 103 transmits a radiographic image to the console 122 via wireless communication with the wireless access point 121.

The radiographic imaging apparatuses 101 to 103 can switch a communication connection between wireless communication and wired communication, depending on use settings in the radiographic imaging room 110 and the instrument carriage 120.

Figure 2:
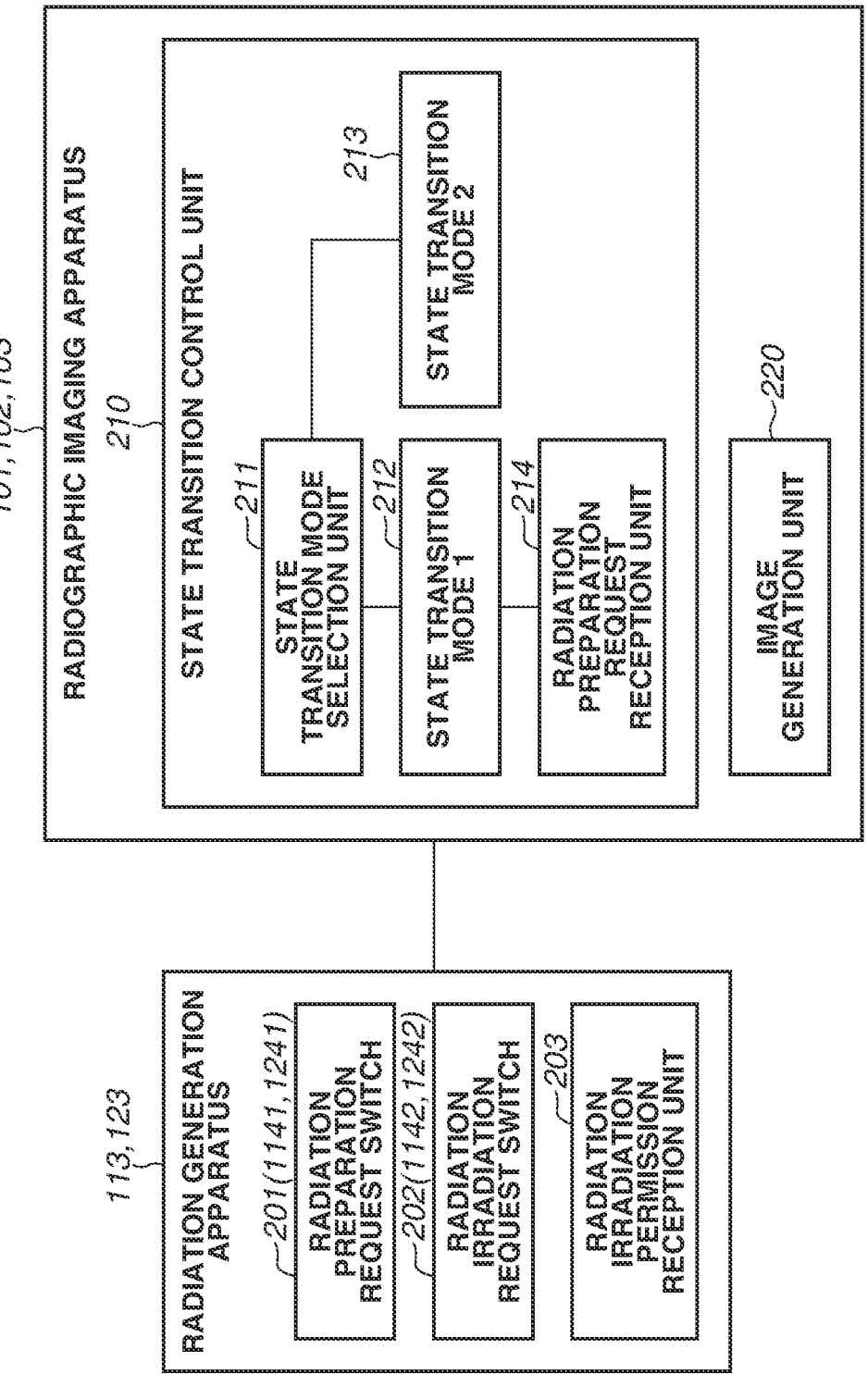
FIG. 2 is a diagram illustrating an example of an internal functional configuration of a radiation generation apparatus and a radiographic imaging apparatus that are illustrated in FIG. 1 according to the first example embodiment.

FIG. 2 is a diagram illustrating an example of an internal functional configuration of the radiation generation apparatuses 113 and 123 and the radiographic imaging apparatuses 101, 102, and 103 illustrated in FIG. 1 according to the first example embodiment of the present disclosure.

The radiation generation apparatuses 113 and 123 include a radiation preparation request switch 201, a radiation irradiation request switch 202, and a radiation irradiation permission reception unit 203 as illustrated in FIG. 2. The radiation preparation request switch 201 is a switch that corresponds to the radiation preparation request switches 1141 and 1241 illustrated in FIG. 1. The radiation irradiation request switch 202 is a switch that corresponds to the radiation irradiation request switches 1142 and 1242 illustrated in FIG. 1.

At the press of the radiation preparation request switch 201, the radiation generation apparatuses 113 and 123 transmit radiation preparation request information to the radiographic imaging apparatuses 101, 102, and 103. At the press of the radiation irradiation request switch 202, the radiation generation apparatuses 113 and 123 transmit radiation irradiation request information to the radiographic imaging apparatuses 101, 102, and 103. When radiation irradiation permission information is received by the radiation irradiation permission reception unit 203 during a ready-for-radiation-irradiation state, the radiation generation apparatuses 113 and 123 perform radiation irradiation.

The radiographic imaging apparatuses 101, 102, and 103 include a state transition control unit 210 and an image generation unit 220 as illustrated in FIG. 2. The state transition control unit 210 switches the radiographic imaging apparatuses 101, 102, and 103 between a stand-by state and a ready-for-imaging state. The power consumption is lower in the stand-by state than in the ready-for-imaging state. The state transition control unit 210 includes a state transition mode selection unit 211, a first state transition mode 212 ("STATE TRANSITION MODE 1" in FIG. 2), a second state transition mode 213 ("STATE TRANSITION MODE 2" in FIG. 2), and a radiation preparation request reception unit 214 as illustrated in FIG. 2.

The radiation preparation request reception unit 214 is a reception unit that receives radiation preparation request information (information including radiation irradiation preparation start information) from the radiation generation apparatuses 113 and 123. The first state transition mode 212 is a state transition mode of cancelling the stand-by state and changing to the ready-for-imaging state based on the radiation irradiation preparation start information, in a case where radiation preparation request information (information including radiation irradiation preparation start information) is received by the radiation preparation request reception unit 214. The second state transition mode 213 is a state transition mode of changing from the stand-by state to the ready-for-imaging state based on other information excluding the radiation preparation request information (information including radiation irradiation preparation start information) received by the radiation preparation request reception unit 214.

The state transition mode selection unit 211 is a selection unit that selects one of the first state transition mode 212 and the second state transition mode 213 based on a state transition characteristic in changing from the stand-by state to the ready-for-imaging state in the radiographic imaging apparatuses 101, 102, and 103 and a radiation irradiation characteristic in changing to the ready-for-radiation-irradiation state in the radiation generation apparatuses 113 and 123. The state transition characteristic is a characteristic including a ready-for-imaging state transition time in changing from the stand-by state to the ready-for-imaging state. The radiation irradiation characteristic is a characteristic including a radiation irradiation preparation time in changing from the stand-by state to the ready-for-radiation-irradiation state. According to the present example embodiment, time information for irradiation preparation by the radiation generation apparatuses 113 and 123 is referred to as "radiation irradiation preparation time". The radiation irradiation preparation time is a time that includes a time up to a time point at which a rotation state of a rotary anode becomes stable and an in-plane distribution of radiation becomes uniform. The radiation irradiation preparation time varies depending on an X-ray tube of the radiation generation apparatuses 113 and 123. The radiation irradiation preparation time in the radiation generation apparatus 123 at the instrument carriage 120 is often longer than the radiation irradiation preparation time in the radiation generation apparatus 113 at the radiographic imaging room 110. Further, according to the present example embodiment, time information about a transition of the radiographic imaging apparatuses 101, 102, and 103 from the stand-by state to the ready-for-imaging state is referred to as "ready-for-imaging state transition time". The ready-for-imaging state transition time includes a time from supply of power to a sensor (sensor 310 in FIG. 3 described below) to a time point at which an electric charge accumulation characteristic becomes stable and there are no longer artifacts. Thus, the transition to the ready-for-imaging state is not immediately after cancellation of the stand-by state and takes a length of time. According to the present example embodiment, the state transition mode selection unit 211 selects the first state transition mode 212 in a case where the radiation irradiation preparation time is longer than the ready-for-imaging state transition time, whereas the state transition mode selection unit 211 selects the second state transition mode 213 in a case where the radiation irradiation preparation time is shorter than or equal to the ready-for-imaging state transition time. According to the present example embodiment, the radiation irradiation characteristic is, for example, a characteristic calculated using the radiation irradiation preparation start information about a start of preparation for irradiation with the radiation in the radiation generation apparatuses 113 and 123 and irradiation preparation completion information about completion of the preparation for irradiation with the radiation in the radiation generation apparatuses 113 and 123.

Figure 3:
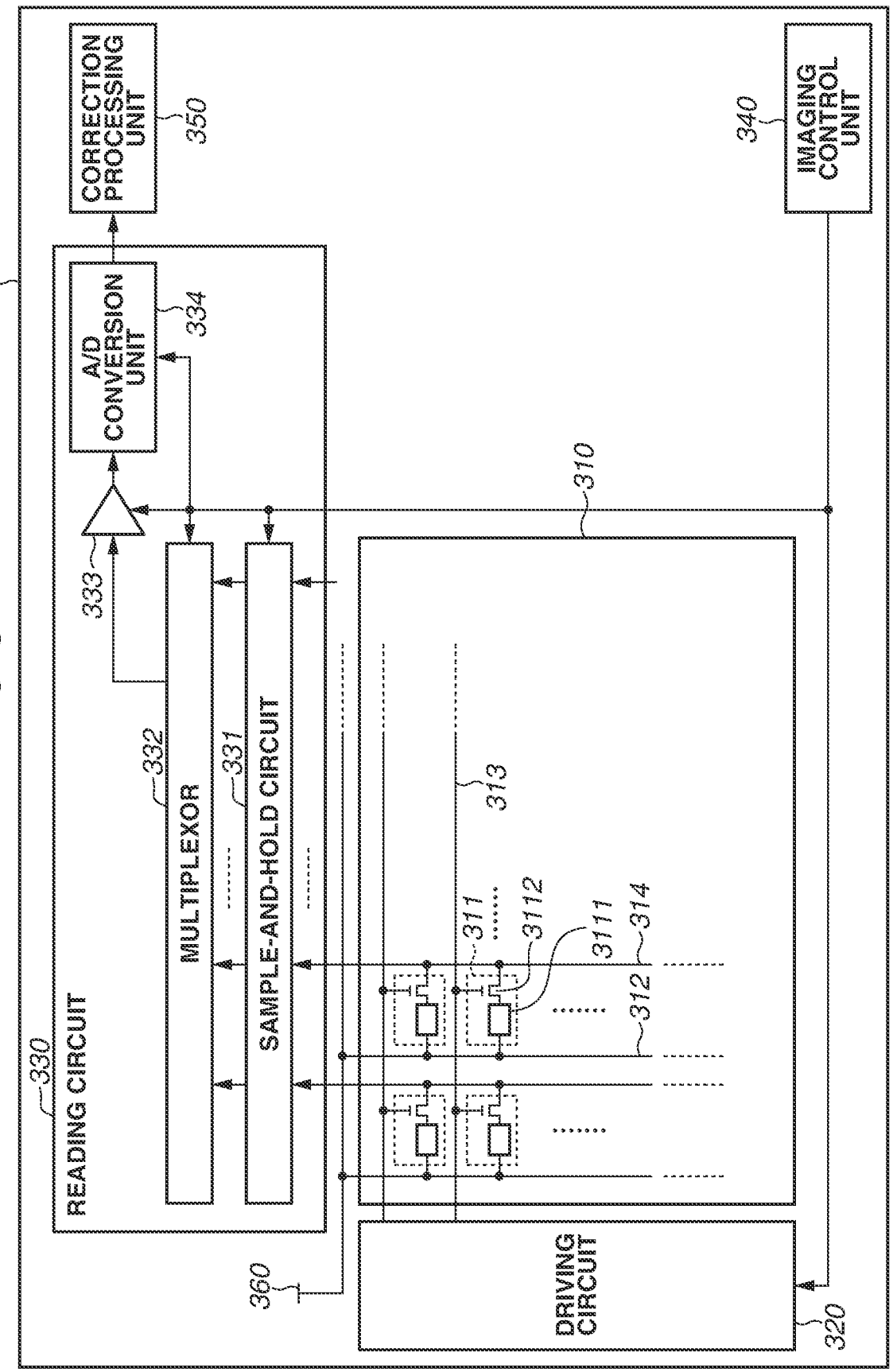
FIG. 3 is a diagram illustrating an example of an internal configuration of an image generation unit illustrated in FIG. 2.

The image generation unit 220 is a component that generates a radiographic image based on incident radiation. FIG. 3 is a diagram illustrating an example of an internal configuration of the image generation unit 220 illustrated in FIG. 2 according to the first example embodiment of the present disclosure. The image generation unit 220 includes the sensor 310, a driving circuit 320, a reading circuit 330, an imaging control unit 340, a correction processing unit 350, and a power unit 360 as illustrated in FIG. 3.

The sensor 310 includes a plurality of pixels 311 arranged in two-dimensional array form including a plurality of rows and a plurality of columns. Each of the plurality of pixels 311 includes a conversion element 3111 and a switch element 3112. The conversion element 3111 converts incident radiation into an electric charge as an electric signal and accumulates the electric charge. The conversion element 3111 can include a scintillator that converts radiation into visible light and a photoelectric conversion element that converts visible light into an electric charge, or the conversion element 3111 can be an element that converts radiation directly into an electric charge. The switch element 3112 transfers the electric charge accumulated in the conversion element 3111 to a signal line 314. The switch element 3112 includes, for example, a transistor, such as a thin film transistor (TFT). The switch element 3112 includes a control terminal. The switch element 3112 is changed to an on-state, conductive state, at supply of an on-state voltage to the control terminal and is changed to an off-state, i.e., non-conductive state, at supply of an off-state voltage to the control terminal. A bias voltage is fed to a terminal of the conversion element 3111 from the power unit 360 via a bias line 312. Another terminal of the conversion element 3111 is connected to the signal line 311 via the switch element 3112. The control terminal of the switch element 3112 is connected to a driving line 313. In the sensor 310, a plurality of the driving lines 313 extending in a row direction (horizontal direction in FIG. 3) is arranged in a column direction (vertical direction in FIG. 3). The control terminals of the switch elements 3112 of the pixels 311 of each row are connected to a corresponding one of the driving lines 313. In the sensor 310, a plurality of the signal lines 314 extending in the column direction is arranged in the row direction.

Main terminals of the switch elements 3112 of the pixels 311 of each column are connected to a corresponding one of the signal lines 314.

The driving circuit 320 drives the sensor 310, based on a control signal fed from the imaging control unit 310. Specifically, the driving circuit 320 feeds a driving signal to the control terminals of the switch elements 3112 via the driving lines 313. The driving circuit 320 feeds the on-state voltage as the driving signal to change the switch element 3112 to the on-state or feeds the off-state voltage as the driving signal to change the switch element 3112 to the off-state. At the change of the switch element 3112 to the on-state, the electric charge accumulated in the conversion element 3111 is transferred to the signal line 314.

The reading circuit 330 reads the electric charge from the sensor 310, based on a control signal fed from the imaging control unit 340 and generates a signal corresponding to the read electric charge. Then, the reading circuit 330 feeds the generated signal to the correction processing unit 350. The reading circuit 330 includes a sample-and-hold circuit 331, a multiplexor 332, an amplifier 333, and an analog/digital (A/D) conversion unit 334 as illustrated in FIG. 3. The sample-and-hold circuit 331 holds the electric charges read from the conversion elements 3111 in units of pixel rows. The multiplexor 332 sequentially extracts the electric charges of the pixels of one row that are held by the sample-and-hold circuit 331, and feeds the extracted electric charges to the amplifier 333. The amplifier 333 amplifies the electric charges fed from the multiplexor 332 and feeds the amplified electric charges to the A/D conversion unit 334. The A/D conversion unit 334 converts an analog signal fed from the amplifier 333 into a digital signal (corresponding to the above-described radiographic image data) and feeds the digital signal to the correction processing unit 350. The correction processing unit 350, for example, acquires a captured image from which unnecessary dark charge components have been removed by dark correction for subtracting dark image data acquired only from dark charge components without radiation irradiation from the radiographic image data converted into a digital value.

Figure 4:
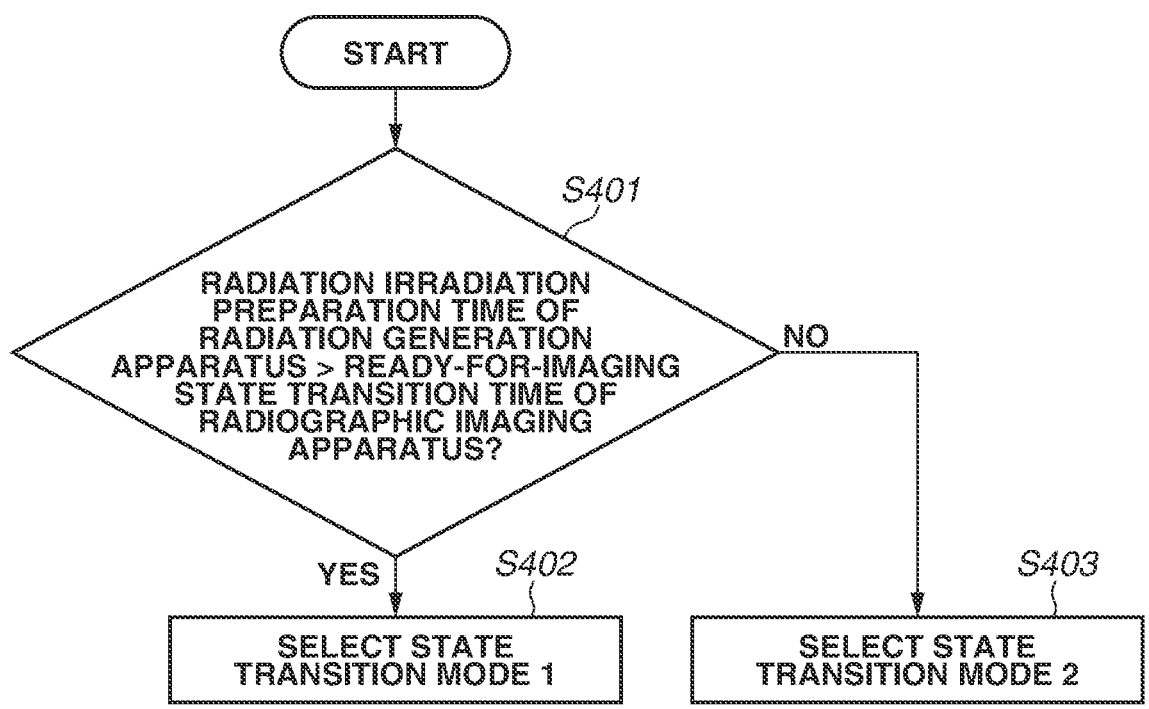
FIG. 4 is a flowchart illustrating an example of a method of controlling the radiographic imaging apparatus according to the first example embodiment.

FIG. 4 is a flowchart illustrating an example of a process of controlling the radiographic imaging apparatuses 101, 102, and 103 according to the first example embodiment of the present disclosure. Specifically, FIG. 4 is a flowchart illustrating an example of a process that is performed by the state transition mode selection unit 211 illustrated in FIG. 2.

In step S401 in FIG. 4, first, the state transition mode selection unit 211 acquires information about the radiation irradiation preparation time and information about the ready-for-imaging state transition time. A method for the acquisition of the radiation irradiation preparation time information is a method in which time information for preparation for irradiation by a radiation generation apparatus that generates radiation for radiographic imaging is set for the radiographic imaging apparatus. Alternatively, the radiographic imaging apparatus can acquire the radiation irradiation preparation time information from the radiation generation apparatus that generates radiation for radiographic imaging, via communication with the radiation generation apparatus. A console or another device can acquire the radiation irradiation preparation time information via communication with the radiation generation apparatus that generates radiation for radiographic imaging, and thereafter the radiation irradiation preparation time information can be acquired from the device that has acquired the radiation irradiation preparation time information. An applicable method for acquisition of the ready-for-imaging state transition time information is, for example, a method using design values at the time of development of the radiographic imaging apparatus or a method of measuring the time of a transition from the stand-by state to the ready-for-imaging state.

Then, the state transition mode selection unit 211 determines whether the radiation irradiation preparation time acquired as information is longer than the ready-for-imaging state transition time.

In a case where the radiation irradiation preparation time is longer than the ready-for-imaging state transition time according to a result of the determination in step S401 (YES in step S401), the processing proceeds to step S402.

In step S402, the state transition mode selection unit 211 performs processing to select the first state transition mode 212 ("STATE TRANSITION MODE 1" in FIG. 2) illustrated in FIG. 2.

On the other hand, in a case where the radiation irradiation preparation time is not longer than (e.g., is shorter than) the ready-for-imaging state transition time according to a result of the determination in step S401 (NO in step S401), the processing proceeds to step S403.

In step S403, the state transition mode selection unit 211 performs processing to select the second state transition mode 213 ("STATE TRANSITION MODE 2" in FIG. 2) illustrated in FIG. 2.

FIG. 5 is a diagram illustrating an example of a timing chart of a case where the radiation irradiation preparation time is shorter than the ready-for-imaging state transition time according to a comparative example to which an aspect of the present invention is not applied. The case of the radiographic imaging room 110 often corresponds to FIG. 5 because the radiation generation apparatus 113 has good performance.

In a case where, for example, the radiation preparation request switch 1141 and the radiation irradiation request switch 1142 are simultaneously pressed as illustrated by "RADIATION PREPARATION REQUEST" and "RADIATION IRRADIATION REQUEST" in FIG. 5, the radiation generation apparatus 113 notifies the radiographic imaging apparatus 101 that a radiation preparation request is generated. At the press of the radiation preparation request switch 1141, the radiation generation apparatus 113 is changed to the ready-for-radiation-irradiation state and transmits a radiation irradiation request to the radiographic imaging apparatus 101.

Then, at receipt of the radiation preparation request from the radiation generation apparatus 113 by the radiation preparation request reception unit 214, the radiographic imaging apparatus 101 cancels the stand-by state and is changed to the ready-for-imaging state. In FIG. 5, since a time 503 from the receipt of the radiation preparation request to the transition to the ready-for-imaging state is longer than a time 502 to the transition to the ready-for-radiation-irradiation state, the radiation irradiation request has been received before the transition to the ready-for-imaging state. Thus, the radiographic imaging apparatus 101 transmits an irradiation permission to the radiation generation apparatus 113, and the radiation generation apparatus 113 performs radiation irradiation. At this time, an irradiation delay 501 from the press of the radiation irradiation request switch 1142 to the radiation irradiation is due to a bottleneck in the ready-for-imaging state of the radiographic imaging apparatus 101.

While the description has been given of the case where the radiation preparation request switch 1141 and the radiation irradiation request switch 1142 are simultaneously pressed, similarly, even in a case of waiting with the radiation preparation request switch 1141 being pressed, the time (system preparation delay) from the press of the radiation preparation request switch 1141 to the completion of preparation by the radiation generation apparatus 113 and the radiographic imaging apparatus 101 is due to a bottleneck in the ready-for-imaging state of the radiographic imaging apparatus 101.

FIG. 6 is a diagram illustrating an example of a timing chart of a case where the radiation irradiation preparation time is longer than the ready-for-imaging state transition time in the radiographic imaging system 100 according to the first example embodiment of the present disclosure. In FIG. 6, the radiation irradiation preparation time is longer than that in FIG. 5, and FIG. 6 is a timing chart of a case where the state transition mode selection unit 211 selects the first state transition mode 212 ("STATE TRANSITION MODE 1" in FIG. 2) illustrated in FIG. 2. A case where a radiographic imaging apparatus is connected to the instrument carriage 120 illustrated in FIG. 1 and communicates with the instrument carriage 120 often corresponds to FIG. 6.

Prior to radiographic imaging, the state transition mode selection unit 211 of, for example, the radiographic imaging apparatus 103 performs processing to select the first state transition mode 212 illustrated in FIG. 2 in a case where the radiation irradiation preparation time is longer than the ready-for-imaging state transition time in FIG. 6. The first state transition mode 212 ("STATE TRANSITION MODE 1" in FIG. 2) in FIG. 2 is a mode in which the stand-by state is cancelled after receipt of a radiation preparation request and power saving is possible.

In a case where, for example, the radiation preparation request switch 1241 and the radiation irradiation request switch 1242 are simultaneously pressed as illustrated by "RADIATION PREPARATION REQUEST" and "RADIATION IRRADIATION REQUEST" in FIG. 6, the radiation generation apparatus 123 notifies the radiographic imaging apparatus 103 that a radiation preparation request is generated.

Then, at receipt of the radiation preparation request from the radiation generation apparatus 123 by the radiation preparation request reception unit 214, the radiographic imaging apparatus 103 cancels the stand-by state and is changed to the ready-for-imaging state. In FIG. 6, since a time 603 from the receipt of the radiation preparation request to the transition to the ready-for-imaging state is shorter than a time 602 to the transition to the ready-for-radiation-irradiation state, the radiation irradiation request has not been received at the time of the transition to the ready-for-imaging state. Then, when the radiation generation apparatus 123 is changed to the ready-for-radiation-irradiation state, the radiation generation apparatus 123 transmits the radiation irradiation request to the radiographic imaging apparatus 103.

At the receipt of the radiation irradiation request from the radiation generation apparatus 123, the radiographic imaging apparatus 103 transmits an irradiation permission to the radiation generation apparatus 123, and then the radiation generation apparatus 123 performs radiation irradiation. At this time, an irradiation delay 601 from the press of the radiation irradiation request switch 1242 to the radiation irradiation is due to a bottleneck in the radiation irradiation preparation time of the radiation generation apparatus 123, and a ready-for-imaging preparation time of the radiographic imaging apparatus 103 does not cause a bottleneck while power consumption of the radiographic imaging apparatus 103 is reduced.

While the description has been given of the case where the radiation preparation request switch 1241 and the radiation irradiation request switch 1242 are simultaneously pressed, the present example embodiment is not limited to the disclosed form. For example, a case where the radiation preparation request switch 1241 and the radiation irradiation request switch 1242 are pressed with a time difference within the radiation irradiation preparation time is also applicable to the present example embodiment. Even in a case of waiting with the radiation preparation request switch 1241 being pressed, the system preparation delay is due to a bottleneck in the radiation irradiation preparation time of the radiation generation apparatus 123, and a ready-for-imaging preparation time of the radiographic imaging apparatus 103 does not cause a bottleneck while the power consumption of the radiographic imaging apparatus 103 is reduced.

Next, a case where the radiographic imaging apparatuses 101 and 102 that are different in the ready-for-imaging state transition time are disposed in the radiographic imaging room 110 in FIG. 1 will be described below. FIG. 7 is a diagram illustrating an example of a timing chart of a case where the radiographic imaging apparatus 101 with a short ready-for-imaging state transition time is used as a radiographic imaging apparatus in the radiographic imaging system 100 according to the first example embodiment of the present disclosure. FIG. 8 is a diagram illustrating an example of a timing chart of a case where the radiographic imaging apparatus 102 with a longer ready-for-imaging state transition time is used as a radiographic imaging apparatus in the radiographic imaging system 100 according to the first example embodiment of the present disclosure.

First, FIG. 7 will be described below. In FIG. 7, prior to radiographic imaging, the state transition mode selection unit 211 of the radiographic imaging apparatus 101 performs processing to select the first state transition mode 212 illustrated in FIG. 2 since the radiation irradiation preparation time is longer than the ready-for-imaging state transition time as illustrated in FIG. 7. The first state transition mode 212 ("STATE TRANSITION MODE 1" in FIG. 2) in FIG. 2 is a mode in which the stand-by state is cancelled at receipt of a radiation preparation request and power saving is possible.

In a case where the radiation preparation request switch 1141 and the radiation irradiation request switch 1142 are simultaneously pressed as illustrated by "RADIATION PREPARATION REQUEST" and "RADIATION IRRADIATION REQUEST" in FIG. 7, the radiation generation apparatus 113 notifies the radiographic imaging apparatus 101 that a radiation preparation request is generated.

Then, at receipt of the radiation preparation request from the radiation generation apparatus 113 by the radiation preparation request reception unit 214, the radiographic imaging apparatus 101 cancels the stand-by state and is changed to the ready-for-imaging state. In FIG. 7, since a time 703 from the receipt of the radiation preparation request to the transition to the ready-for-imaging state is shorter than a time 702 to the transition to the ready-for-radiation-irradiation state, the radiation irradiation request has not been received at the time of the transition to the ready-for-imaging state. Then, when the radiation generation apparatus 113 is changed to the ready-for-radiationirradiation state, the radiation generation apparatus 113 transmits the radiation irradiation request to the radiographic imaging apparatus 101.

At the receipt of the radiation irradiation request from the radiation generation apparatus 113, the radiographic imaging apparatus 101 transmits an irradiation permission to the radiation generation apparatus 113, and then the radiation generation apparatus 113 performs radiation irradiation. At this time, an irradiation delay 701 from the press of the radiation irradiation request switch 1142 to the radiation irradiation is due to a bottleneck in the radiation irradiation preparation time of the radiation generation apparatus 113, and the ready-for imaging preparation time of the radiographic imaging apparatus 101 does not causes a bottleneck.

While the description has been given of the case where the radiation preparation request switch 1141 and the radiation irradiation request switch 1142 are simultaneously pressed, the present example embodiment is not limited to the disclosed form. For example, a case where the radiation preparation request switch 1141 and the radiation irradiation request switch 1142 are pressed with a time difference within the radiation irradiation preparation time is also applicable to the present example embodiment. Even in a case of waiting with the radiation preparation request switch 1141 being pressed, the system preparation delay is due to a bottleneck in the radiation irradiation preparation time of the radiation generation apparatus 113, and the ready-for-imaging preparation time of the radiographic imaging apparatus 101 does not cause a bottleneck while the power consumption of the radiographic imaging apparatus 101 is reduced.

Next, FIG. 8 will be described below. In FIG. 8, prior to radiographic imaging, the state transition mode selection unit 211 of the radiographic imaging apparatus 102 performs processing to select the second state transition mode 213 illustrated in FIG. 2 since the radiation irradiation preparation time is shorter than the ready-for-imaging state transition time as illustrated in FIG. 8. The second state transition mode 213 ("STATE TRANSITION MODE 2" in FIG. 2) in FIG. 2 is a mode that consumes more electric power to cancel the stand-by state at receipt of an imaging preparation request from the console 112 but reduces the irradiation delay.

An instruction to use the radiographic imaging apparatus 102 is issued by operating the console 112. At this time, the console 112 transmits an imaging preparation request to the radiographic imaging apparatus 102. Then, the state transition mode selection unit 211 of the radiographic imaging apparatus 102 performs processing to select the second state transition mode 213 in FIG. 2 since a radiation irradiation preparation time 802 of the radiation generation apparatus 113 for use in imaging is shorter than a ready-for-imaging state transition time 803. At the receipt of the imaging preparation request, the radiographic imaging apparatus 102 cancels the stand-by state. At this time, the time from the cancellation of the stand-by state to the transition to the ready-for-imaging state is the ready-for-imaging state transition time 803.

In a case where the radiation preparation request switch 1141 and the radiation irradiation request switch 1142 are simultaneously pressed as illustrated by "RADIATION PREPARATION REQUEST" and "RADIATION IRRADIATION REQUEST" in FIG. 8, the radiation generation apparatus 113 starts changing to the ready-for-radiation-irradiation state. Then, when the radiation generation apparatus 113 is changed to the ready-for-radiation-irradiation state, the radiation generation apparatus 113 transmits a radiation irradiation request to the radiographic imaging apparatus 102. Then, since the radiographic imaging apparatus 102 is in the ready-for-imaging state, at the receipt of the imaging preparation request from the radiation generation apparatus 113, the radiographic imaging apparatus 102 transmits an irradiation permission to the radiation generation apparatus 113, and then the radiation generation apparatus 113 performs radiation irradiation. At this time, an irradiation delay 801 from the press of the radiation irradiation request switch 1142 to the radiation irradiation is due to a bottleneck in the radiation irradiation preparation time of the radiation generation apparatus 113, and the ready-for-imaging preparation time of the radiographic imaging apparatus 102 does not cause a bottleneck.

While the description has been give of the case where the radiation preparation request switch 1141 and the radiation irradiation request switch 1142 are simultaneously pressed, the present example embodiment is not limited to the disclosed form. For example, a case where the radiation preparation request switch 1141 and the radiation irradiation request switch 1142 are pressed with a time difference within the radiation irradiation preparation time is also applicable to the present example embodiment. Even in a case of waiting with the radiation preparation request switch 1141 being pressed, the system preparation delay is due to a bottleneck in the radiation irradiation preparation time of the radiation generation apparatus 113, and the ready-for-imaging preparation time of the radiographic imaging apparatus 102 does not cause a bottleneck.

While the description has been given of the example where the radiographic imaging apparatus 102 cancels the stand-by state at the receipt of the imaging preparation request, the stand-by state can be cancelled by pressing a switch of the radiographic imaging apparatus 102 or by pressing a switch of a different device associated with the radiographic imaging apparatus 102. While the description has been give of the example where an instruction to use the radiographic imaging apparatus 102 is issued by operating the console 112, the imaging preparation request can be transmitted in a case where an order to image is selected by the console 112, a specific button is pressed, or a specific operation is performed. The state transition mode can be changed by comparing the radiation irradiation preparation time and the ready-for-imaging state transition time in a case where an irradiation condition of a radiation X-ray tube connected to the radiation generation apparatus 113 or an X-ray tube voltage is changed. While FIGS. 7 and 8 illustrate the example where the radiographic imaging apparatuses 101 and 102 are switched in the radiographic imaging room 110, the radiographic imaging apparatuses that are connected to the instrument carriage 120 can be switched.

In the radiographic imaging apparatus according to the first example embodiment, the state transition mode selection unit 211 selects one of the first state transition mode 212 and the second state transition mode 213, based on the state transition characteristic in the transition of the radiographic imaging apparatus from the stand-by state to the ready-for-imaging state and the radiation irradiation characteristic in the transition of the radiation generation apparatus that generates radiation for radiographic imaging to the ready-for-radiation-irradiation state.

With the foregoing configuration, a stand-by state cancellation method that is optimum in terms of power consumption is selected, in a case where a plurality of stand-by state cancellation methods is available in the radiographic imaging apparatus.

Next, a second example embodiment of the present disclosure will be described below. Redundant descriptions of similarities between the second example embodiment of the present disclosure and the first example embodiment described above are omitted, and differences between the second example embodiment and the first example embodiment will be described below.

A schematic configuration of a radiographic imaging system according to the second example embodiment is similar to that of the radiographic imaging system 100 according to the first example embodiment illustrated in FIG. 1. Further, internal functional configurations of the radiation generation apparatuses 113 and 123 and the radiographic imaging apparatuses 101, 102, and 103 according to the second example embodiment are similar to those of the radiation generation apparatuses 113 and 123 and the radiographic imaging apparatuses 101, 102, and 103 according to the first example embodiment illustrated in FIG. 2.

FIG. 9 is a flowchart illustrating an example of a method of controlling the radiographic imaging apparatuses 101, 102, and 103 according to the second example embodiment of the present disclosure. Specifically, FIG. 9 is a flowchart illustrating an example of a process performed by the state transition mode selection unit 211 illustrated in FIG. 2. An example where the radiographic imaging apparatus 102 is applied as a radiographic imaging apparatus will be described below with reference to the flowchart in FIG. 9.

In step S901 in FIG. 9, first, the radiographic imaging apparatus 102 (e.g., the state transition mode selection unit 211) acquires information about the radiation irradiation preparation time and information about the ready-for-imaging state transition time and stores the acquired information. The information about the radiation irradiation preparation time is time information for preparation for irradiation by the radiation generation apparatus 113. The information about the ready-for-imaging state transition time information is time information for changing of the radiographic imaging apparatus 102 from the stand-by state to the ready-for-imaging state. Then, the state transition mode selection unit 211 of the radiographic imaging apparatus 102 determines whether the radiation irradiation preparation time acquired as information is longer than the ready-for-imaging state transition time.

In a case where the radiation irradiation preparation time is longer than the ready-for-imaging state transition time according to a result of the determination in step S901 (YES in step S901), the processing proceeds to step S902.

In step S902, the state transition mode selection unit 211 of the radiographic imaging apparatus 102 determines whether there is external power supply.

In a case where there is no external power supply according to a result of the determination in step S902 (NO in step S902), the processing proceeds to step S903.

In step S903, the state transition mode selection unit 211 of the radiographic imaging apparatus 102 performs processing to select the first state transition mode 212 ("STATE TRANSITION MODE 1" in FIG. 2) illustrated in FIG. 2 to reduce the power consumption.

On the other hand, in a case where the radiation irradiation preparation time is not longer than (e.g., is shorter than) the ready-for-imaging state transition time according to a result of the determination in step S901 (NO in step S901) or in a case where there is external power supply according to a result of the determination in step S902 (YES in step S902), the processing proceeds to step S904.

In step S904, the state transition mode selection unit 211 of the radiographic imaging apparatus 102 performs processing to select the second state transition mode 213 ("STATE TRANSITION MODE 2" in FIG. 2) illustrated in FIG. 2. The longer the time from the cancellation of the stand-by state to the radiographic imaging, the less the noise in a captured image, and consequently a radiographic image with greater image quality is acquired. In light of this point, in a case where there is external power supply, the image quality of a radiographic image is often prioritized over a request to reduce power consumption, and therefore the control is effective.

The timing of the case where the first state transition mode 212 ("STATE TRANSITION MODE 1" in FIG. 2) is selected is similar to that in the timing charts illustrated in FIGS. 6 and 7 according to the first example embodiment, so that redundant descriptions thereof are omitted. Further, the timing of the case where the second state transition mode 213 ("STATE TRANSITION MODE 2" in FIG. 2) is selected is similar to that in the timing chart illustrated in FIG. 8 according to the first example embodiment. Thus, redundant descriptions thereof are omitted.

In the above-described radiographic imaging apparatuses according to the second example embodiment, the state transition mode selection unit 211 selects the first state transition mode 212 in a case where the radiation irradiation preparation time is longer than the ready-for-imaging state transition time (YES in step S901) and there is no external power supply (NO in step S902), whereas the state transition mode selection unit 211 selects the second state transition mode 213 in a case where the radiation irradiation preparation time is shorter than or equal to the ready-for-imaging state transition time (NO in step S901) or in a case where the radiation irradiation preparation time is longer than the ready-for-imaging state transition time (YES in step S901) and there is external power supply (NO in step S902).

With the foregoing configuration, in a case where a plurality of stand-by state cancellation methods is available in the radiographic imaging apparatus, a stand-by state cancellation method that is optimum in terms of power consumption is selected, and also a stand-by state cancellation method for a characteristic of great image quality of a radiographic image is selected.

Next, a third example embodiment of the present disclosure will be described below. Redundant descriptions of similarities between the third example embodiment of the present disclosure and the first and second example embodiments described above are omitted, and differences between the third example embodiment and the first and second example embodiments will be described below.

A schematic configuration of a radiographic imaging system according to the third example embodiment is similar to that of the radiographic imaging system 100 according to the first example embodiment illustrated in FIG. 1. Further, internal functional configurations of the radiation generation apparatuses 113 and 123 and the radiographic imaging apparatuses 101, 102, and 103 according to the third example embodiment are similar to those of the radiation generation apparatuses 113 and 123 and the radiographic imaging apparatuses 101, 102, and 103 according to the first example embodiment illustrated in FIG. 2.

A method by which the radiographic imaging apparatus 101 acquires information about the radiation irradiation preparation time that is time information for preparation for irradiation by the radiation generation apparatus 113 according to the third example embodiment will be described below with reference to FIG. 10. FIG. 10 is a diagram illustrating an example of a timing chart of the radiographic imaging system 100 according to the third example embodiment of the present disclosure.

In a case where the radiation preparation request switch 1141 and the radiation irradiation request switch 1142 are simultaneously pressed as illustrated by "RADIATION PREPARATION REQUEST" and "RADIATION IRRADIATION REQUEST" in FIG. 10, the radiation generation apparatus 113 notifies the radiographic imaging apparatus 101 that a radiation preparation request is generated.

Then, the radiographic imaging apparatus 101 operates a timer to measure an elapsed time from receipt of the radiation preparation request from the radiation generation apparatus 113. When the radiation generation apparatus 113 is changed to the ready-for-radiation-irradiation state, the radiation generation apparatus 113 notifies the radiographic imaging apparatus 101 that a radiation irradiation request is generated.

At receipt of the radiation irradiation request from the radiation generation apparatus 113, the radiographic imaging apparatus 101 checks the timer and measures a time 1001 from the receipt of the radiation preparation request to obtain the radiation irradiation preparation time. In the method illustrated in FIG. 10, the radiation irradiation preparation time is measured at installation of the radiographic imaging apparatus 101, and. after the measurement, the state transition mode of the radiographic imaging apparatus 101 is selected by the method according to the first or second example embodiment.

While the description has been give of the case where the radiation preparation request switch 1141 and the radiation irradiation request switch 1142 are simultaneously pressed, the present example embodiment is not limited to the disclosed form. For example, a case where the radiation preparation request switch 1141 and the radiation irradiation request switch 1142 are pressed with a time difference within the radiation irradiation preparation time is also applicable to the present example embodiment.

Next, a fourth example embodiment of the present disclosure will be described below. Redundant descriptions of similarities between the fourth example embodiment of the present disclosure and the first to third example embodiments described above are omitted, and differences between the fourth example embodiment and the first to third example embodiments will be described below.

A schematic configuration of a radiographic imaging system according to the fourth example embodiment is similar to that of the radiographic imaging system 100 according to the first example embodiment illustrated in FIG. 1. Further, internal functional configurations of the radiation generation apparatuses 113 and 123 and the radiographic imaging apparatuses 101, 102, and 103 according to the fourth example embodiment are similar to those of the radiation generation apparatuses 113 and 123 and the radiographic imaging apparatuses 101, 102, and 103 according to the first example embodiment illustrated in FIG. 2.

A method by which the radiographic imaging apparatus 101 acquires information about the radiation irradiation preparation time that is time information for preparation for irradiation by the radiation generation apparatus 113 according to the fourth example embodiment will be described below with reference to FIG. 11. FIG. 11 is a diagram illustrating an example of a timing chart of the radiographic imaging system 100 according to the fourth example embodiment of the present disclosure.

First, according to the fourth example embodiment, the radiographic imaging apparatus 101 is changed to an irradiation detection mode of detecting radiation irradiation and is changed to a ready-for-radiation-irradiation-detection state.

Then, in a case where the radiation preparation request switch 1141 and the radiation irradiation request switch 1142 are simultaneously pressed as illustrated by "RADIATION PREPARATION REQUEST" and "RADIATION IRRADIATION REQUEST" in FIG. 11, the radiation generation apparatus 113 notifies the radiographic imaging apparatus 101 that a radiation preparation request is generated.

Then, the radiographic imaging apparatus 101 operates the timer to measure an elapsed time from receipt of the radiation preparation request from the radiation generation apparatus 113. Since the radiation irradiation request switch 1142 is pressed at the time of transition to the ready-for-radiation-irradiation state, the radiation generation apparatus 113 performs radiation irradiation.

Then, at detection of irradiation with radiation from the radiation generation apparatus 113, the radiographic imaging apparatus 101 checks the timer and measures a time 1101 from the receipt of the radiation preparation request to obtain the radiation irradiation preparation time. In the method illustrated in FIG. 11, as in the third example embodiment, the radiation irradiation preparation time is measured at installation of the radiographic imaging apparatus 101, and after the measurement, the state transition mode of the radiographic imaging apparatus 101 is selected by the method according to the first or second example embodiment.

While the case where the radiation preparation request switch 1141 and the radiation irradiation request switch 1142 are simultaneously pressed is disclosed, the present example embodiment is not limited to the disclosed form. For example, a case where the radiation preparation request switch 1141 and the radiation irradiation request switch 1142 are pressed with a time difference within the radiation irradiation preparation time is also applicable to the present example embodiment.

According to the fourth example embodiment, a characteristic calculated using the irradiation preparation start information about a start of preparation for irradiation with the radiation by the radiation generation apparatus 113 and radiation irradiation detection information is applicable to the radiation irradiation characteristic. At this time, according to the fourth example embodiment, the radiation irradiation detection information can be information acquired from a signal notifying a state of the radiation generation apparatus 113 or can be information acquired by detecting radiation by the radiographic imaging apparatus 101.

Embodiments of the present disclosure are also realized by the following process. Specifically, a program for realizing one or more functions of the above-described example embodiments is fed to a system or an apparatus via a network or a storage medium, and one or more processors of a computer of the system or the apparatus reads the program and executes the read program. Further, embodiments of the present disclosure are also realized by a circuit (e.g., application-specific integrated circuit (ASIC)) that realizes one or more functions.

The program and a computer-readable storage medium storing the program are also included in the scope of the present invention.

The above-described example embodiments of the present disclosure are mere examples of implementation of the present invention, and the technical scope of the present invention should not be interpreted narrowly. In other words, various forms of implementation of the present invention are possible without departing from the technical concept or major feature of the present invention.

Other Embodiments

Embodiment(s) of the present disclosure can also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While example embodiments, it is to be understood that the invention is not limited to the disclosed example embodiments. The scope of the following claims is to be accorded the broadest interpretation so as to encompass all such modifications and equivalent structures and functions.

This application claims the benefit of Japanese Patent Application No. 2020-160942, filed Sep. 25, 2020, which is hereby incorporated by reference herein in its entirety.

What is claimed is:

1. A radiographic imaging apparatus including an image generation unit configured to generate a radiographic image based on incident radiation, the radiographic imaging apparatus comprising:
a reception unit configured to receive irradiation preparation start information about a start of preparation for irradiation with the radiation in a radiation generation apparatus that generates the radiation; and
a selection unit configured to select a state transition mode from among a first state transition mode of changing from a stand-by state to a ready-for-imaging state based on the irradiation preparation start information and a second state transition mode of changing from the stand-by state to the ready-for-imaging state based on other information excluding the irradiation preparation start information, the selection unit selecting the state transition mode based on a state transition characteristic in changing from the stand-by state in which power consumption is lower than power consumption in the ready-for-imaging state to the ready-for-imaging state in the radiographic imaging apparatus and a radiation irradiation characteristic in changing to a ready-for-radiation-irradiation state in the radiation generation apparatus.

2. The radiographic imaging apparatus according to claim 1, wherein the state transition characteristic is a characteristic including a ready-for-imaging state transition time in changing from the stand-by state to the ready-for-imaging state.

3. The radiographic imaging apparatus according to claim 1, wherein the radiation irradiation characteristic is a characteristic including a radiation irradiation preparation time in changing from the stand-by state to the ready-for-radiation-irradiation state.

4. The radiographic imaging apparatus according to claim 1,
wherein the state transition characteristic is a characteristic including a ready-for-imaging state transition time in changing from the stand-by state to the ready-for-imaging state,
wherein the radiation irradiation characteristic is a characteristic including a radiation irradiation preparation time in changing from the stand-by state to the ready-for-radiation-irradiation state, and
wherein in a case where the radiation irradiation preparation time is longer than the ready-for-imaging state transition time, the selection unit selects the first state transition mode, and in a case where the radiation irradiation preparation time is shorter than or equal to the ready-for-imaging state transition time, the selection unit selects the second state transition mode.

5. The radiographic imaging apparatus according to claim 1,
wherein the state transition characteristic is a characteristic including a ready-for-imaging state transition time in changing from the stand-by state to the ready-for-imaging state,
wherein the radiation irradiation characteristic is a characteristic including a radiation irradiation preparation time in changing from the stand-by state to the ready-for-radiation-irradiation state, and
wherein in a case where the radiation irradiation preparation time is longer than the ready-for-imaging state transition time and there is no external power supply, the selection unit selects the first state transition mode, and in a case where the radiation irradiation preparation time is shorter than or equal to the ready-for-imaging state transition time or in a case where the radiation irradiation preparation time is longer than the ready-for-imaging state transition time and there is external power supply, the selection unit selects the second state transition mode.

6. The radiographic imaging apparatus according to claim 1, wherein the radiation irradiation characteristic is a characteristic calculated using the irradiation preparation start information about the start of preparation for irradiation with radiation in the radiation generation apparatus and irradiation preparation completion information about completion of preparation for irradiation with the radiation in the radiation generation apparatus.

7. The radiographic imaging apparatus according to claim 1, wherein the radiation irradiation characteristic is a characteristic calculated using the irradiation preparation start information about the start of preparation for irradiation with the radiation in the radiation generation apparatus and irradiation detection information about detection of irradiation with the radiation.

8. The radiographic imaging apparatus according to claim 7, wherein the irradiation detection information is information acquired from a signal notifying a state of the radiation generation apparatus.

9. The radiographic imaging apparatus according to claim 7, wherein the irradiation detection information is information acquired by detecting the radiation in the radiographic imaging apparatus.

10. A radiographic imaging system comprising:
the radiographic imaging apparatus according to claim 1; and
the radiation generation apparatus.

11. A method of controlling a radiographic imaging apparatus including an image generation unit configured to generate a radiographic image based on incident radiation, the method comprising:
receiving irradiation preparation start information about a start of preparation for irradiation with the radiation in a radiation generation apparatus that generates the radiation; and
selecting a state transition mode from among a first state transition mode of changing from a stand-by state to a ready-for-imaging state based on the irradiation preparation start information and a second state transition mode of changing from the stand-by state to the ready-for-imaging state based on other information excluding the irradiation preparation start information, the state transition mode being selected based on a state transition characteristic in changing from the stand-by state in which power consumption is lower than power consumption in the ready-for-imaging state to the ready-for-imaging state in the radiographic imaging apparatus and a radiation irradiation characteristic in changing to a ready-for-radiation-irradiation state in the radiation generation apparatus.

12. A non-transitory computer-readable storage medium storing a program that causes a radiographic imaging apparatus to perform the method according to claim 11.

* * * * *